(12) United States Patent
Blass

(10) Patent No.: US 6,325,626 B1
(45) Date of Patent: Dec. 4, 2001

(54) INTERDENTAL BRUSH

(75) Inventor: Jacob Moses Blass, London (GB)

(73) Assignee: Westone Products Limited (GB)

( * ) Notice: Subject to any disclaimer, the term of this patent is extended or adjusted under 35 U.S.C. 154(b) by 0 days.

(21) Appl. No.: 09/627,419

(22) Filed: Jul. 27, 2000

(30) Foreign Application Priority Data

Nov. 8, 1999 (GB) .................................................. 9926418

(51) Int. Cl.⁷ ........................................................ A61C 3/00
(52) U.S. Cl. ........................ 433/141; 132/321; 15/167.1
(58) Field of Search ..................... 132/321, 308, 132/309; 433/141; 15/167.1

(56) References Cited

U.S. PATENT DOCUMENTS

| | | |
|---|---|---|
| 2,624,062 | 1/1953 | Knoderer . |
| 3,078,856 * | 2/1963 | Bender et al. ........................ 132/321 |
| 4,030,199 | 6/1977 | Russell . |
| 4,387,479 | 6/1983 | Kigyos . |
| 4,691,404 | 9/1987 | Tarrson et al. . |
| 4,710,996 | 12/1987 | Tarrson et al. . |
| 4,780,923 | 11/1988 | Schultheiss . |
| 5,029,358 | 7/1991 | Zimmerman . |
| 5,394,584 | 3/1995 | Breitschmid . |
| 5,488,751 * | 2/1996 | Gekhter et al. ...................... 15/167.1 |
| 5,630,244 * | 5/1997 | Chang .................................. 15/167.1 |
| 5,775,346 | 7/1998 | Szyszkowski . |
| 5,860,183 * | 1/1999 | Kam .................................... 15/167.1 |
| 5,926,899 * | 7/1999 | Scott .................................... 15/167.1 |
| 5,934,295 | 8/1999 | Gekhter et al. . |
| 6,192,544 * | 2/2001 | Persidsky et al. ................... 15/167.1 |

FOREIGN PATENT DOCUMENTS 672 723    12/1989   (CH) .

* cited by examiner

*Primary Examiner*—Todd E. Manahan
(74) *Attorney, Agent, or Firm*—Larson & Taylor, PLC

(57) ABSTRACT

An interdental brush has an elongate handle and a brush portion projecting from its front end. The handle has a main body which maintains the shape of the handle and is made of a first material and, at its front end, a body of elastomeric material softer than said first material which provides the front end surface of the handle. This reduces risk of pain or damage to a user's gums.

11 Claims, 3 Drawing Sheets

Figure 5:
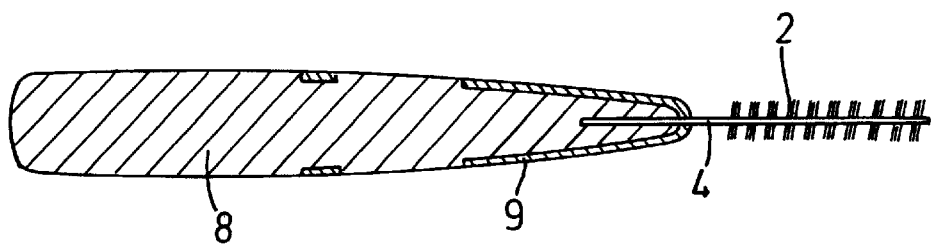

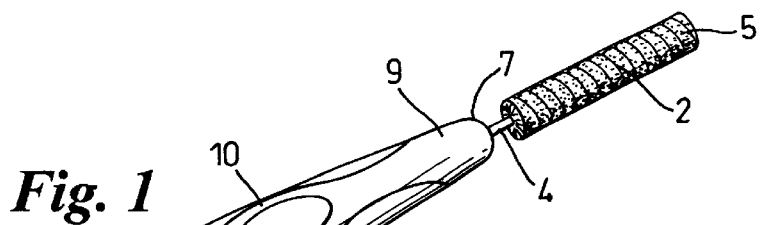
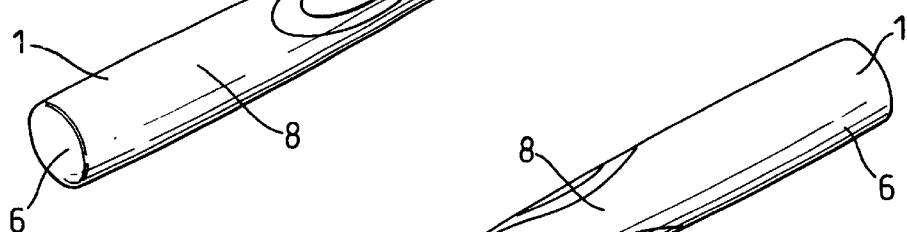
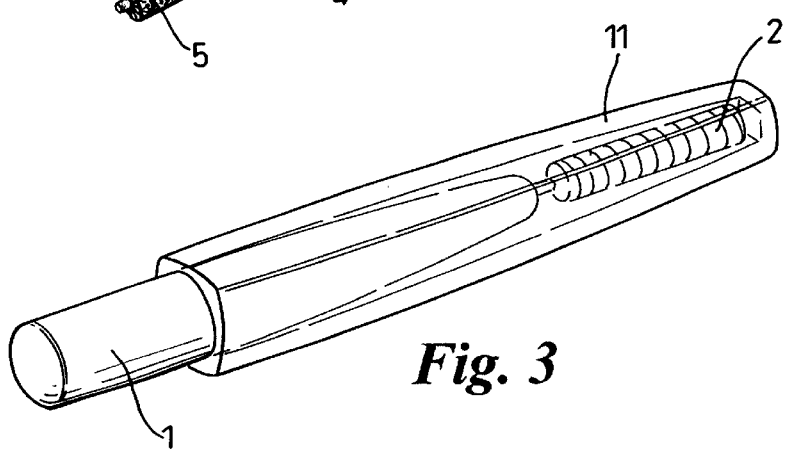
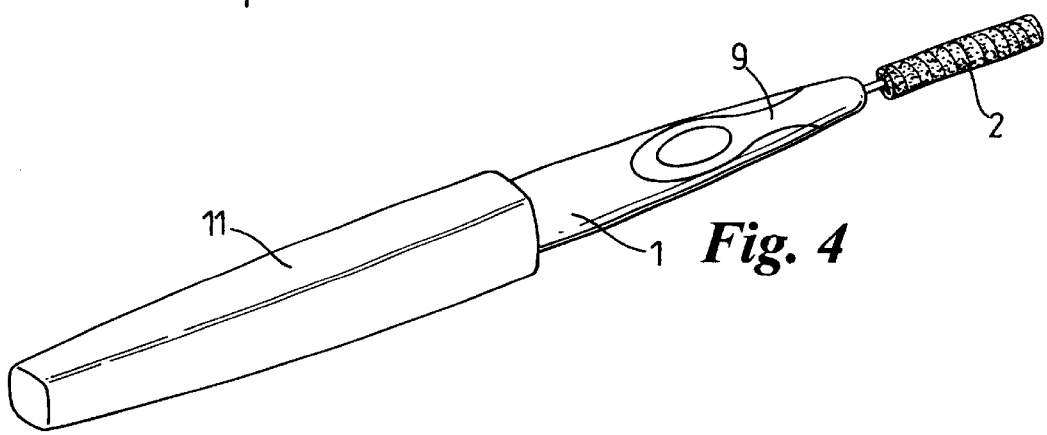

INTERDENTAL BRUSH

FIELD OF THE INVENTION

This invention relates to interdental brushes. An interdental brush is used in dentistry and at home to clean in the interdental spaces, i.e. the spaces between adjacent teeth.

DESCRIPTION OF THE PRIOR ART

Typically, an interdental brush has a handle by which it is held by its user and a brush portion projecting from one end of the handle. It is common for the handle to be made of moulded hard plastics material, and the brush portion to have a spine of twisted wires which hold bristles projecting radially from the spine. U.S. Pat. No. 4,691,404 describes an interdental brush having a handle made of a mixture of thermoplastic elastomer and a general purpose polypropylene. A brush element having a twisted wire stem which is moulded in the handle. The handle has a bottle nose end, with a neck receiving the wire stem. This neck portion has a flexing and resilient capability to allow the user to control the angle at which the brush projects at will.

Because an interdental brush typically has a short life, it should be made cheaply. The present inventor has further perceived that the use of a hard plastics material for the handle has a disadvantage that, if it is accidentally pushed hard against the gums of the user, it is liable to cause pain and even tissue damage.

SUMMARY OF THE INVENTION

According to the present invention there is provided an interdental brush having an elongate handle and a brush portion projecting from a front end of the handle in the elongation direction of the handle, wherein said handle has a main body which maintains the shape of the handle and is made of a first material and at least part of the end surface of the handle at the front end is provided by a body of an elastomeric material softer than said first material. Preferably this body of elastomeric material provides the whole tip surface at the front end of the handle. The body of elastomeric material may be a surface layer, or may be a body of material providing the whole thickness of the handle at the front end.

The main body part of the handle is typically of moulded plastics material and is sufficiently rigid to maintain the shape and structure of the handle and to anchor the brush portion, while the body of elastomeric material, which is secured on the main body part, is softer. Suitable elastomeric materials are natural rubber and synthetic elastomeric materials such as polyalkenes, e.g. EPDM. This material may be foamed.

The body of elastomeric material acts as a cushion, so that when the user accidentally pushes the handle hard against the gum, there is less risk of pain and tissue damage.

In one form of the invention the handle has a dome-shaped front end from which the spine of the brush portion projects, at least the surface of this dome-shaped end being provided by the body of elastomeric material.

The body of elastomeric material may extend rearwardly from the front end of the handle as a surface layer of the handle. This can have several functions. It can help to secure the body of elastomeric material on the handle, it can assist the user in gripping the brush during use and it can provide the brush with an attractive appearance, particularly if the elastomeric material has a different colour from the material of the remainder of the handle. It may also assist in the holding of a removable cap to the handle, by increasing the frictional interaction with the internal surface of the cap.

In one preferred embodiment, the front end of the handle has a bottle-nose shape. The bottle-nose shape may comprise an elongate neck portion of the handle having a core of material harder than the elastomeric material, the body of elastomeric material providing a surface layer on the core at least at the front end of the bottle-nose shape, and the brush portion may have brushing material for contact with the teeth during use and a spine holding the brushing material, the spine extending within the core. Preferably the core containing the spine is bendable substantially non-resiliently by the user so that the brush portion adopts and maintains a selectable orientation with respect to the handle.

BRIEF INTRODUCTION OF THE DRAWINGS

Figure 6:
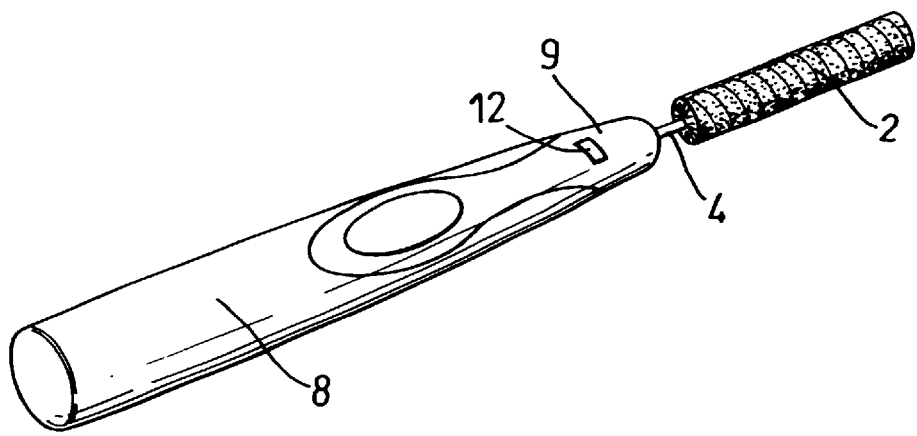
Figure 7:
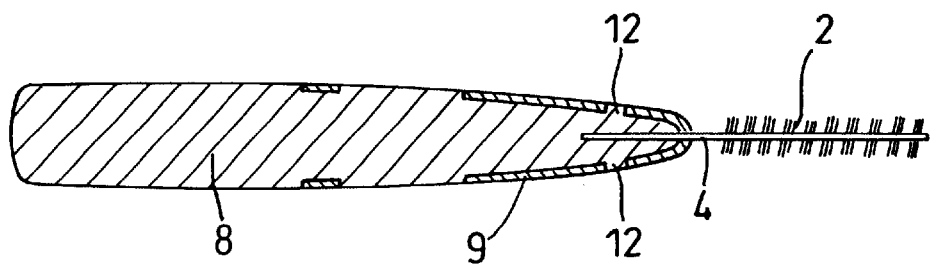
Figure 8:
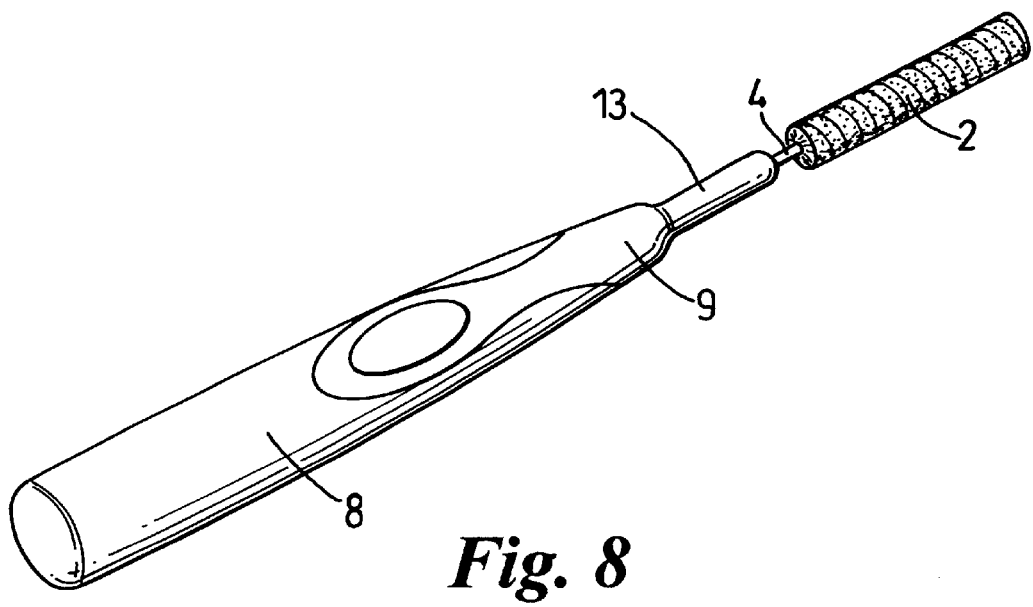
Figure 9:
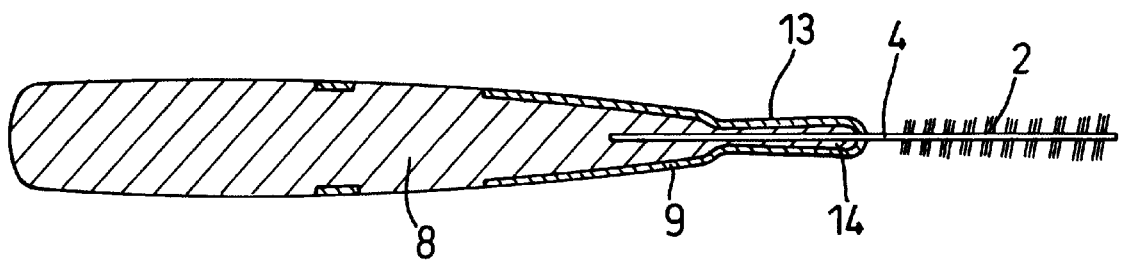

Embodiments of the invention will now be described by way of non-limitative example, with reference to the accompanying drawings, in which:

FIG. 1 is a first perspective view of a first interdental brush according to the invention, FIG. 2 is a second perspective view, from a different direction, of the interdental brush of FIG. 1, FIG. 3 is a view corresponding to FIG. 1, showing additionally a cap of the brush in its storage position, FIG. 4 is a view corresponding to FIG. 1 showing the cap in a position which it may be placed during use of the brush, FIG. 5 is an axial cross-section of the interdental brush of FIGS. 1 to 4, FIG. 6 is a perspective view of a modified form of the interdental brush of FIGS. 1 to 5, FIG. 7 is an axial sectional view of the interdental brush of FIG. 6, corresponding to the view of FIG. 5, FIG. 8 is a perspective view of a second interdental brush according to the invention, and FIG. 9 is an axial sectional view of the interdental brush of FIG. 8.

DESCRIPTION OF THE PREFERRED EMBODIMENTS

The brush embodying the invention shown in the drawing has a handle 1, a brush portion 2 and, as an additional optional component shown in FIGS. 3 and 4, a cap 3. The brush portion 2 is shown schematically, and may in conventional manner consist of a spine 4 of twisted wires and a bristle portion 5 of radially projecting bristles anchored in the twisted wires of the spine portion.

The spine 4 projects rearwardly from the bristle portion into the handle 1 and is anchored in the material of the handle by in situ moulding. The handle 1 has a wide rear end portion 6 and gradually tapers along its length towards its front end 7 which has a dome-shape with the spine 4 projecting from the centre of the dome. The handle is of circular transverse cross-section, and consists of a main body portion 8 made of moulded white hard synthetic plastics material, such as polypropylene or polycarbonate. At the dome-shaped front end 7 this body portion 8 is covered by an elastomeric layer 9 which is for example of a darker colour than the body portion 8 to provide an attractive appearance.

The layer 9 entirely covers the dome end 7 providing the whole of the end surface facing towards the bristle portion 5. The layer 9 extends rearwardly covering the whole of the body portion over a length of preferably between 3 and 8 mm from the front end, and extends further rearwardly as looped strips 10 along the handle 1 at each of opposite sides of the body portion 8, so that where the handle is gripped by the fingers of the user, the surface of the handle is partly provided by the layer 9 and partly by the harder surface of the body portion 8. This assists the gripping of the handle by the user and gives the handle a pleasant feel and appearance for the user.

As mentioned above, the covering of the tip of the handle 1 by elastomeric material 9, which is chosen to be relatively soft and yielding, compared with the harder material of the body portion 8, gives the user protection against pain and injury to the gums, if the brush is accidentally pushed so that the handle contacts the gums.

The interdental brush embodying the invention and shown in FIGS. 1 to 5 is made by insert moulding, by two-stage injection moulding. First, with the metal spine 4 projecting into the mould space, the hard main body portion 8 of the handle is moulded, being made for example of polypropylene or polycarbonate. Secondly, in the same or a different mould the elastomeric layer 9 is moulded onto the body portion 8. The layer 9 is for example a thermoplastic elastomer, such as Santoprene (trade name). Other manufacturing methods and materials are available. The thickness of the layer 9 is about 1 mm, and is preferably in the range 0.5 to 2 mm.

FIGS. 3 and 4 show a cap 11 which may optionally be sold and used together with the interdental brush. The cap 10 has an exterior shape which is not cylindrical but has corners to give it a pleasant appearance and help a user to grip it. This shape prevents rolling of the cap when put down on a surface (for the same reason the handle 1 may be non-circular in section, to avoid rolling). The interior surface of the cap is cylindrical in transverse section and tapering, and as can be seen in FIG. 4 has dimensions so that adjacent its mouth 11 it grips the handle 1 so that the cap remains in place on the handle in both positions shown in FIGS. 3 and 4. When in the storage position shown in FIG. 3, the tip end of the handle 1 and the brush portion 2 remain out of contact with the cap, which protects them. At its closed end, the cap has a small aperture so that air can escape when the cap is pushed onto the handle. As shown in FIG. 4, the handle can be pushed onto the cap from the other end, to provide an extension of the handle 1, during use of the brush. The cap 11 can be made of opaque synthetic plastics material, typically the same plastics material as the handle 1, but preferably is of translucent or transparent material.

In a modification, the brush of FIGS. 1 to 5 is double-ended, i.e. with brush portions 2 projecting at both ends of the handle 1 and elastomeric layers 9 covering both tips of the handle.

The length of the spine 4 carrying the bristles is typically about 1 cm, and is suitably in the range 0.5 to 2 cm. The length of the handle is suitably in the range 3 to 7 cm.

The modified form of the interdental brush shown in FIGS. 6 and 7, is identical to that of FIGS. 1 to 5, except that, to assist in the anchoring of the elastomeric layer 9 to the body portion 8, the body portion 8 has two keying projections 12 on opposite sides which project through the layer 9 to the surface of the handle. These projections 12 are elongate in the circumferential direction around the handle.

The interdental brush embodying the invention shown in FIGS. 8 and 9 is generally the same as that of FIGS. 1 to 5 and is manufactured in the manner described above, except that the front end of the handle 8 has a bottle-nose shape with an elongate neck portion 13 projecting forwardly in the axial or elongation direction of the handle, to the tip end at the front end of the handle. The elongate neck 13 is constituted by a core 14 which is a forward extension of the body portion and the layer 9 which extends over the whole surface of the core 14. The moulded-in spine 4 extends along the axis of the core portion 14.

As well as providing the advantages discussed above, the embodiments of FIGS. 8 and 9 allows the user to deform the neck 13 of the handle to bring the brush axis to a selected desired orientation with respect to the handle of the brush. Many users will find it convenient to re-orient the brush with respect to the handle for obtaining access to particular interdental gaps in the mouth. In this embodiment, the neck portion is deformable substantially non-resiliently, but without rupture, so as to allow the user to fix a desired orientation of the brush relative to the handle (provided that the user does not excessively deform or repeatedly deform the neck portion 13). The deformation in this manner of the spine 4 within the neck portion 13 is advantageous, compared with the alternative of bending of a portion of the spine outside the handle 8. Bending of the spine outside the handle tends to cause opening of the twisted wires from each other, so that the bristles of the brush tend to fall out. In the embodiment of FIGS. 8 and 9, the twisted wires of the spine 4 at the deformed portion within the neck portion 13 are held by the material of the handle, so that they cannot open. The bristles are retained in the brush. Preferably the gap between the rearmost end of the bristle portion and the extreme front end of the handle (surface layer 9) is less than 2 mm. The length of the neck 13 may be in the region 0.5 to 1.5 cm. In the embodiment disclosed it is about 1 cm.

It has also been found that, in the brush with a domed front end of the handle, in FIGS. 1 to 7, the front end may be non-resiliently deformed to re-orient the brush portion by the user, due to the rubber layer 9.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

What is claimed is:

1. An interdental brush having an elongate handle having a front end and a brush portion projecting from said front end, wherein said handle has a main body which maintains the shape of the handle and is made of a first material, and said brush portion has a spine of twisted wires and bristles protruding from said spine, said spine being embedded in said front end of the handle, wherein the handle has, at said front end thereof, a second body which is made of a second material which is an elastomeric material softer than said first material, said second body being carried by said main body and providing at least part of the front end surface of said handle at said front end and wherein said spine of the brush portion extends through said second body and is embedded in said main body.

2. An interdental brush according to claim 1, wherein said main body is an elongate body of moulded synthetic plastics material which holds and supports said body of elastomeric material.

3. An interdental brush according to claim 2, wherein said second body is moulded in situ on said body of synthetic resin material.

4. An interdental brush according to claim 1, wherein said front end of said handle has a dome shape.

5. An interdental brush according to claim 1, wherein said front end of said handle has a bottle-nose shape.

6. An interdental brush according to claim 5, wherein said bottle-nose shape comprises an elongate neck portion of said handle having a core of material harder than said elastomeric material, said second body providing a surface layer on said core at least at the extreme end of said bottle-nose shape, and wherein said spine of said brush portion extends within said core.

7. An interdental brush according to claim 6, wherein said core containing said spine is bendable substantially non-resiliently by the user so that the brush portion adopts and maintains a selectable orientation with respect to the handle.

8. An interdental brush according to claim 1, wherein said front end of said handle is bendable substantially non-resiliently by the user so that the brush portion adopts and maintains a selectable orientation with respect to the handle.

9. An interdental brush according to claim 1, wherein said second body extends rearwardly from said front end of said handle as a surface layer of said handle.

10. An interdental brush having an elongate handle having a tapering front end and a brush portion projecting from said front end, wherein said handle has a main body formed of a first material and a layer which is made of a second material which is an elastomeric material softer than the first material, said layer providing at least part of the front end surface of the handle at said front end and wherein said front end of the handle is bendable substantially non-resiliently by the user so that the brush portion adopts and maintains a selectable orientation with respect to the handle.

11. An interdental brush having an elongated handle having a front end and a brush portion projecting from said front end, wherein said handle has a main body which maintains the shape of the handle and is made of a first material and at said front end thereof, a body of elastomeric material softer than said first material which provides at least part of the end surface of said handle at said front end, and wherein, said handle having a core of material harder than said elastomeric material, said body of elastomeric material providing a surface layer on said core at least at the front end of the handle, and wherein said spine extending within said core, and wherein said core containing said spine is bendable substantially non-resiliently by the user so that the brush portion adopts and maintains a selectable orientation with respect to the handle.

* * * * *